United States Patent [19]

Giovanoni

[11] Patent Number: 5,037,655

[45] Date of Patent: Aug. 6, 1991

[54] METHOD OF STABILIZING TRETINOIN

[76] Inventor: Richard L. Giovanoni, 220 Richmond St., E. Taunton, Mass. 02718

[21] Appl. No.: 510,832

[22] Filed: Apr. 18, 1990

[51] Int. Cl.$^5$ .................................................. A61F 2/00
[52] U.S. Cl. .................................... 424/427; 424/333; 514/546; 514/557; 568/824
[58] Field of Search ................ 424/427, 333; 514/557, 514/546; 568/824

[56] References Cited

U.S. PATENT DOCUMENTS

| | | | |
|---|---|---|---|
| 3,906,108 | 9/1975 | Felty | 514/560 |
| 4,022,913 | 3/1977 | Newmark | 514/546 |
| 4,034,114 | 7/1977 | Yu | 514/703 |
| 4,247,547 | 1/1981 | Marks | 424/81 |
| 4,254,100 | 3/1981 | Keller | 514/557 |
| 4,840,970 | 6/1989 | Ohasi | 514/725 |

OTHER PUBLICATIONS

Merck Index 10th Ed., p. 8064 (1983).

*Primary Examiner*—Thurman K. Page
*Assistant Examiner*—William E. Benston, Jr.
*Attorney, Agent, or Firm*—Watson, Cole, Grindle & Watson

[57] ABSTRACT

A tretinoin-mineral oil-petrolatum product in which the ingredients are blended at about 90° C., which product retains its therapeutic activity despite storage at ambient conditions without the need for an antioxidant.

10 Claims, No Drawings

METHOD OF STABILIZING TRETINOIN

FIELD OF THE INVENTION

This invention relates generally to the field of stabilizing vitamins and other therapeutic ingredients against undesirable oxidation. More specifically, it relates to a method of stabilizing tretinoin and the product so stabilized.

BACKGROUND OF THE INVENTION

Tretinoin, also called all-trans retinoic acid or Vitamin A Acid, is derived from Vitamin A by two oxidative steps. The first converts Vitamin A, which is an alcohol, to its aldehyde form while the second, subsequent oxidation converts the terminal carbon aldehyde group to a carboxylic acid group. The agent thus formed is known as Vitamin A Acid or all-trans retinoic acid, or simply tretinoin. The reactions are illustrated as:

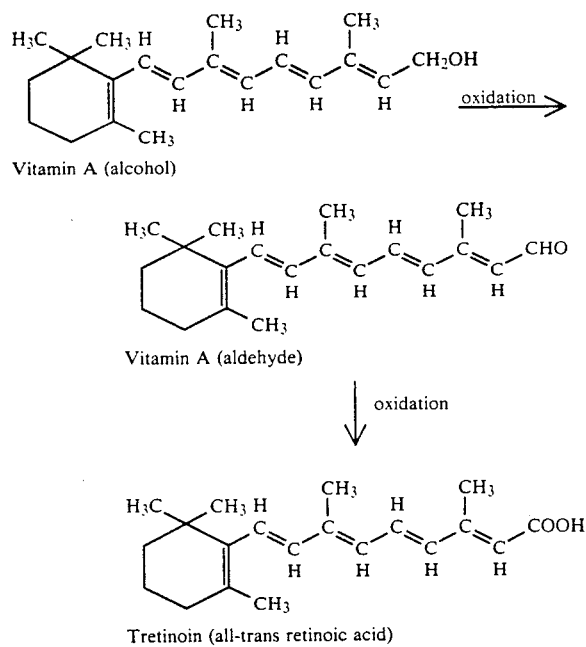

Chemically, oxidation consists of a loss of electrons; reduction is the opposite: a gain of electrons. The oxidative process can involve atmospheric oxygen directly. Additionally, oxidation may also occur by a loss of electrons and without the addition or presence of oxygen in the final product, e.g., oxidation of ferrous chloride to ferric chloride.

Both types of reactions are important, but those involving atmospheric oxygen are more frequently encountered with pharmaceutical or cosmetic products. Oxidative reactions may involve both aqueous and non-aqueous ("oily") formulations. Generally, oxidative reactions depend on several factors such as:

(a) temperature
(b) labile oxygen concentration, "labile oxygen" being considered oxygen that is readily releasable from its bound form;
(c) catalysts that may be present, sometimes as formulation necessities,
(d) pH,
(e) light, and
(f) concentration of the oxidizable ingredients.

In sealed containers a reduction in the oxidative rate can be attained by lowering the temperature for most agents susceptible to oxidative degradation. The pH of the formulation is sometimes critical, since a number of oxidation-reduction processes are dependent upon hydrogen or hydroxyl ions and/or their ratio to one another.

Light often accelerates an oxidation process; storage of the finished product in dark containers frequently does much to retard oxidative reactions. Oxidative photolytic changes in some compounds create degradation by-products which function to propagate or catalyze the decomposition once started. Similar events, termed auto-oxidation, may occur even in the absence of light when susceptible materials are stored in the presence of air. The oxygen concentration of formulations (versus atmospheric oxygen) is a critical factor in many cases and often depends on the temperature of storage. Oxygen becomes more soluble in aqueous media as the temperature is lowered. Thus, oxygen dependent, oxidative reactions can sometimes proceed more rapidly at lower temperatures. Decomposition by oxidation often is a complicated process, with the overall rate dependent upon several factors, the relative importance of each being a function of the particular agent susceptible to oxidative degradation.

Tretinoin is an agent that is extremely sensitive to oxidative degradation, partially due to its high degree of unsaturation. Consequently, it easily undergoes rapid oxidation at ambient conditions. This ease of oxidation is a decided disadvantage, since continued degradation of tretinoin results in a total loss of its topically applied, therapeutic activity. Additionally, the oxidative lability of tretinoin has historically restricted its number dosage form.

Specifically, tretinoin is most susceptible to the following oxidative factors:

(a) ultraviolet or fluorescent lighting
(b) oxygen (atmospheric or labile), and
(c) temperature.

Of these factors, temperature per se appears to be the least critical since it requires at least one of the other factors to be present in order for it to exert significant degradation. Light, alone, or oxygen (atmospheric or labile) is capable of rapid, significant oxidation of tretinoin. Obviously, as the number of degradative factors concurrently present increases, so does the totality and rate of tretinoin's oxidative degradation, and loss of therapeutic efficacy.

In order to stabilize tretinoin in a dosage form suitable for topical application, it has been known to do one or all of the following procedures:

(a) package the tretinoin-containing formulation in light resistant containers;
(b) exclude air from randomly contacting the finished product;
(c) formulate carrier vehicles for the tretinoin so as to exclude labile, oxygen containing ingredients whenever possible;
(d) label the finished product so that it is stored within refrigerated conditions or conditions that mimick same and,
(e) most importantly and most commonly, to include additives (antioxidants) in the formulation that retard oxidative degradation.

Procedures (a) and (b) are most commonly accomplished by (1) packaging the formulation in metal or plastic threaded containers that seal tightly and preclude light, and (2) filling the formulation in the absence of air under yellow light, respectively.

The use of antioxidants has long been practiced to retard oxidation of tretinoin. Typical antioxidants used to retard tretinoin oxidation for topical application dosage forms have included:
  (a) metallic sulfite salts, e.g., sodium sulfite and sodium metabisulfite;
  (b) cresol or toluene derivatives, e.g., benzoic acid, sodium benzoate, calcium benzoate, and butylatedhydroxytoluene;
  (c) ascorbic acid;
  (d) maleic acid;
  (e) propyl gallate, and
  (f) sodium formaldehyde sulfoxylate.

With the possible exception of ascorbic acid, which does not lend itself for topical ophthalmic use due to its pH, all the listed antioxidants have been implicated with serious, sometimes irreversible cytotoxic reactions, viz., liver carcinoma in the case of the toluene and metallic sulfite salts. Consequently, the elimination of such antioxidants by a method that preserves the stability of tretinoin over a reasonable time period is advantageous.

The literature is extensive with documentation that application of topical products to intact dermis results in systemic absorption of the inactive formulation components (such as antioxidants) as well as active ingredients. When the integrity of the dermis is pathologically compromised, the systemic uptake of product ingredients is significantly enhanced.

Systemic uptake of formulation ingredients through topical application by the ophthalmic route is likewise extensively documented. Uptake is exhibited from both aqueous and oleaginous based formulations. The juxtaposition of a large number of blood vessels at the location where ophthalmics are applied favors rapid and significant systemic absorption of all formulation ingredients. As with compromised dermis, this absorption is greatly enhanced during pathologies of the eye and associated areas. An additional concern occasioned by the inclusion of antioxidant materials in ophthalmic preparations is their interference with the healing process associated with ocular tissue. Contemporary ophthalmological literature stresses the need to eliminate anti-microbial preservatives and other ancillary "pharmaceutical necessities" from ophthalmic medications whenever possible because of their demonstrated inhibition of the healing process.

If topical application of a product containing such antioxidants is practiced chronically and/or if the product is applied to large areas of the dermis, the uptake of these agents can be substantial with the potential consequence of severe, systemic, cytotoxic reactions.

It is, therefore, a primary object of this invention to attain a method of manufacture whereby tretinoin can be incorporated into a nonaqueous vehicle in such a fashion that it retains an acceptable range of potency over a reasonable time period—no less than about two years—without the use of antioxidants and without the need for refrigeration of the finished product. To avoid refrigeration promotes better patient compliances and does not limit geographical use of the product to those more affluent areas of the world where refrigeration is commonplace.

Topical application of tretinoin is indicated for at least two major pathological categories. Topical application to the dermis has proved beneficial for treatment of those surface eruptions and skin discolorations attributed to acne vulgaris and psoriasis. Topical application to the surface of the eye has been demonstrated to reverse the spread of certain selective surface disorders, such as corneal and conjunctival keratinization, which leads to irreversible blindness.

SUMMARY OF THE INVENTION

As conceived, the present invention takes the form of both a method of stabilizing tretinoin in tropical dosage form, and the stabilized tretinoin composition. In a broad form the method encompasses heating a formula amount of mineral oil in a first closed vessel, excluding oxygen from the vessel, blending a formula amount of tretinoin with the mineral oil until the tretinoin has been dissolved therein, heating a formula amount of petrolatum in a second closed vessel from which oxygen has been excluded, blending the tretinoin-mineral oil solution and petrolatum while maintaining a substantially oxygen-free atmosphere, cooling the mixture to ambient, and recovering the formula product. As used in this method, formula amounts are those of the final product: 0.0001 to 1.0% tretinoin, 8 to 80% mineral oil, and 20 to 92% petrolatum. This formula amount defines the product of the invention.

An improvement of my inventive method includes heating the mineral oil in a first enclosed vessel to a temperature of about 85 to 95° C., preferably about 90° C. In like manner, the petrolatum is heated in the second vessel to a temperature of about 85 to 95° C., preferably about 90° C. In maintaining a substantially oxygen-free atmosphere in each of the vessels in which the mineral oil and petrolatum are heated, an atmosphere of nitrogen or carbon dioxide is advantageously present. Regarding the product invention, most preferably the product comprises 0.1% tretinoin, 10% mineral oil, and 89.9% white petrolatum for dermal use, and 0.01 tretinoin and 89.99% white petrolatum for ophthalmic usage. As so formulated, the product is in the form of an ointment.

DETAILED DESCRIPTION OF THE INVENTION

As stated in the summary of the invention hereinbefore, the amount of ingredients present in the product are: tretinoin, 0.0001 to 1.0%, mineral oil, 8 to 80%, and white petrolatum 20 to 92%. The most preferred formula for ophthalmic use is tretinoin 0.1%, mineral oil 10% and white petrolatum 89.9%. All compounds are USP grade. All percentages are by weight.

Further, the tretinoin should meet all current USP/NF compendial requirements. The mineral oil preferably exhibits 67 centistokes of viscosity, with an acceptable range of about 67-75 centistokes and a specific gravity of 0.845 to 0.905. It, too, shall meet all current USP/NF compendial requirements. The white petrolatum preferably has a specific gravity of 0.815 to 0.880 and also meets all current USP/NF compendial requirements.

The presently preferred method of manufacture includes a series of steps, all of which should preferably be performed in a yellow light environment. The formula amount of mineral oil is transferred to a closed heating vessel and heated to 90° C. While the temperature is rising, air is purged from the vessel and replaced, preferably with medical grade nitrogen. While maintaining the temperature in a nitrogen environment, the formula amount of tretinoin is added to the vessel and blended until completely dissolved.

Upon total dissolution of the tretinoin in the mineral oil, the mixture is transferred to another closed blending vessel which has an atmosphere of medical grade nitrogen and contains the formula amount of white petrolatum, which has been heated to the preferred temperature of about 90° C. The mixture of three ingredients is blended in the second vessel until a solution or ointment phase is formed, according to the amounts of mineral oil and white petrolatum used. Blending is carried out in a nitrogen atmosphere.

If the final product is not to be sterilized, the in-process mixture may be reheated to or maintained at about 90° C. and passed through a suitable sieve filter, then filled into a suitable container, again under a nitrogen atmosphere. If the final product is to be sterilized, the in-process mixture may be reheated to or maintained at about and passed through a previously sterilized filter having a porosity of not more than about 0.22 microns, and thereafter filled into previously sterilized containers in a nitrogen environment.

The final product is cooled to ambient and, as packaged, contains no effective amount of an antioxidant therein. Despite the absence of such an antioxidant, the product has been found highly resistant to oxidation when stored under ambient conditions and without refrigeration. It has been found that it may be so stored without substantial loss of therapeutic activity for a period of at least about two years. Even after such a period of storage at ambient, the product may be applied to the dermis or the eye, with the well-known therapeutic advantages of Vitamin A Acid.

While the present invention has been described with reference to a preferred embodiment thereof, it will be understood by those of skill in the art that various modifications and alterations may be made both to the product and method of manufacture without departing from the spirit of the invention. As to all such alterations and modifications, it is desired that they be included within the purview of my invention, which is to be limited only by the scope, including equivalents, of the following, appended claims.

I claim:

1. A method of stabilizing tretinoin in topical dosage form, comprising performing the following steps in the substantial absence of water:
   heating a formula amount of mineral oil in a first closed vessel,
   excluding oxygen from said vessel,
   blending a formula amount of tretinoin with said mineral oil until said tretinoin has been dissolved in said mineral oil,
   heating a formula amount of petrolatum in a second closed vessel from which oxygen is excluded,
   blending said tretinoin-mineral oil solution and said petrolatum while maintaining a substantially oxygen-free atmosphere, and
   cooling said mixture to ambient and recovering a formula product substantially free of water comprising about 0.0001 to 1.0% tretinoin, 8 to 80% mineral oil, and 20 to 92% petrolatum, said product being highly resistant to oxidation of said tretinoin but being substantially free of an effective amount of anti-oxidant therein.

2. A method of stabilizing tretinoin as claimed in claim 1, in which said mineral oil is heated in said first closed vessel to a temperature of about 85 to 95° C.

3. A method of stabilizing tretinoin as claimed in claim 2, in which said mineral oil is heated to a temperature of about 90° C.

4. A method of stabilizing tretinoin as claimed in claim 1, in which said petrolatum is heated in said second vessel to a temperature of about 85 to 95° C.

5. A method of stabilizing tretinoin as claimed in claim 4, in which said petrolatum is heated to a temperature of about 90° C.

6. A method of stabilizing tretinoin as claimed in claim 1, in which said tretinoin is dissolved in said mineral oil while maintaining a nitrogen or carbon dioxide atmosphere in said first vessel.

7. A method of stabilizing tretinoin as claimed in claim 1, in which said mineral oil-tretinoin mixture is blended with said petrolatum in said second vessel in an atmosphere of nitrogen or carbon dioxide.

8. A method of stabilizing tretinoin in topical dosage form for ophthalmic use, comprising performing the following steps in the substantial absence of water:
   heating a formula amount of mineral oil in a first closed vessel,
   maintaining an atmosphere of nitrogen or carbon dioxide in said vessel,
   blending a formula amount of tretinoin with said mineral oil until said tretinoin has been dissolved in said mineral oil,
   heating a formula amount of petrolatum in a second closed vessel,
   maintaining a nitrogen or carbon dioxide atmosphere in said second vessel,
   blending said tretinoin-mineral oil mixture into said petrolatum in said second vessel, and
   cooling said mixture to ambient and recovering a formula product substantially free of water comprising about 0.01% tretinoin, 10% mineral oil and 89.99% petrolatum, said product being highly resistant to oxidation of said tretinoin and being substantially free of an effective amount of anti-oxidant therein.

9. A method of stabilizing tretinoin as claimed in claim 2, in which said mineral oil is heated in said first closed vessel to a temperature of about 90° C.

10. A method of stabilizing tretinoin as claimed in claim 4, in which said petrolatum is heated in said second closed vessel to a temperature of about 90° C.

* * * * *